(12) United States Patent
Von Alfthan

(10) Patent No.: US 7,537,376 B2
(45) Date of Patent: May 26, 2009

(54) DEVICE FOR A CONTINUOUSLY OPERATED DILUTING OF A SLURRY SAMPLE

(75) Inventor: Christian Von Alfthan, Espoo (FI)

(73) Assignee: Outotec Oyj, Espoo (FI)

( * ) Notice: Subject to any disclaimer, the term of this patent is extended or adjusted under 35 U.S.C. 154(b) by 707 days.

(21) Appl. No.: 10/543,011

(22) PCT Filed: Feb. 4, 2004

(86) PCT No.: PCT/FI2004/000055

§ 371 (c)(1),
(2), (4) Date: Jul. 22, 2005

(87) PCT Pub. No.: WO2004/070357

PCT Pub. Date: Aug. 19, 2004

(65) Prior Publication Data

US 2006/0050272 A1 Mar. 9, 2006

(30) Foreign Application Priority Data

Feb. 5, 2003 (FI) .................................. 20030173

(51) Int. Cl.
*B01F 5/04* (2006.01)
(52) U.S. Cl. .................... 366/142; 366/143; 366/167.1; 366/177.1
(58) Field of Classification Search ................. 366/142, 366/143, 165.1, 165.4, 173.1, 177.1, 167.1
See application file for complete search history.

(56) References Cited

U.S. PATENT DOCUMENTS 2,306,962 A * 12/1942 Kropp ...................... 366/165.1
4,021,021 A * 5/1977 Hall et al. ................. 366/156.1
4,056,324 A   11/1977 Göhde
4,684,251 A   8/1987 Brouwer et al.
5,311,290 A   5/1994 Olson et al.
6,286,376 B1  9/2001 Davidson et al.

FOREIGN PATENT DOCUMENTS

| DE | 4005061 | 8/1990 |
|----|---------|--------|
| EP | 0604307 | 6/1994 |
| FI | 57662 | 6/1976 |
| FI | 110033 | 1/2000 |
| GB | 2095827 | 10/1982 |
| WO | WO 03/46518 | 6/2003 |

* cited by examiner

*Primary Examiner*—David L Sorkin
(74) *Attorney, Agent, or Firm*—Locke Lord Bissel & Liddell, LLP

(57) ABSTRACT

This invention relates to a device for a continuously operated dilution of a slurry sample, through which device the slurry sample is fed directly into a continuously operated optical analyzer, such as a grain size analyzer. The device comprises elements for feeding the slurry sample, elements for feeding diluting liquid and elements for removing solids contained in the slurry, as well as elements for discharging both the liquid contained in the slurry and the liquid used for dilution. The device of the invention comprises at least one downwardly narrowing chamber (2, 31) that is connected to the analyzer measurement cell (3, 34) so that two opposite walls (10, 32) of the chamber (2, 31) are essentially parallel both with respect to each other and with respect to the respective walls (21, 35) of the measurement cell (3, 34).

7 Claims, 4 Drawing Sheets

DEVICE FOR A CONTINUOUSLY OPERATED DILUTING OF A SLURRY SAMPLE

This application is the national phase application under 35 U.S.C. §371 of International application No. PCT/FI2004/000055; filed on Feb. 4, 2004, entitled, "DEVICE FOR A CONTINUOUSLY OPERATED DILUTING OF A SLURRY SAMPLE" which claims the benefit of Finish Patent Application No. 20030173; filed on Feb. 5, 2003.

The present invention relates to a device for a continuously operated diluting of a slurry sample, through which device the slurry sample is fed directly to a continuously operated optical analyzer, such as a grain size analyzer.

In the analysis of slurry samples, certain measurements, such as optical grain size measurements, require that the solids contained in the slurry samples is diluted down to a tenth or even to a hundredth part of the original content. From the U.S. Pat. No. 6,286,376, there is known a particle size analyzer where a slurry sample is conducted onto an inclined surface, from which water fed in as a continuous flow washes the sample away, simultaneously diluting it. The initially diluted sample is diluted further with water continuously supplied in a funnel, from which the diluted sample is conducted, by making use of gravity, along a conduit to a particle size analyzer. Said conduit may include a mixing chamber, to which water is likewise continuously supplied in order to further dilute the sample. The diluting steps of said U.S. Pat. No. 6,286,376; are carried out in separate dilution units that are interconnected by intermediation of conduits.

The object of the present invention is to eliminate some of the drawbacks of the prior art and to achieve an improved device that is more secure in operation for diluting a slurry sample in continuous operation, through which device the slurry sample can be directly fed into a continuously operated analyzer, such as an optical grain size analyzer. The essential novel features of the invention are enlisted in the appended claims.

According to the invention, from the slurry flow to be analyzed, there is extracted a sample by a sampling device, and said sample is diluted in the device according to the invention prior to conducting it into analysis, advantageously for instance in an optically operated grain size analyzer. From the slurry flow to be analyzed, there is extracted a solids-containing sample preferably by a sample cutter in an essentially continuous operation. The obtained slurry sample flow is conducted into a diluting device, compiled of one or several, advantageously two, downwardly narrowing and mechanically interconnected chambers that are in liquid contact and at least partly filled with liquid such as water. In an embodiment with two chambers, the solids-containing slurry sample to be analyzed is fed into the first chamber, the supply chamber, and the solids to be analyzed are removed from the diluting device according to the invention through the second chamber, the discharge chamber. When using one chamber in the diluting chamber according to the invention, the chamber serves both as a supply chamber and a discharge chamber.

In the diluting device according to the invention, the sample slurry flow is conducted from the sample cutter serving as the sampler to an inclined surface arranged in the open top part of the diluting device. The inclined surface is advantageously aligned so that the inclined surface is positioned, throughout the operation of the diluting device, above the surface of the liquid contained in the diluting device. However, the inclined surface may also be at least partly covered by the liquid fed in the chamber. At the bottom part, the diluting device is attached to a measurement cell, made of a transparent material, of the continuously operated analyzer, such as an optical grain size analyzer, so that the cross-sectional area of the discharge aperture placed in the bottom part of the diluting device essentially corresponds to the cross-sectional area of the measurement cell having the shape of a rectangular prism. In addition, two opposite walls of the diluting device walls connected to the discharge aperture of the diluting device are installed in parallel with respect to each other, advantageously in the vertical direction, and so that said opposite walls are further parallel and essentially equal in width also with the corresponding walls of the measurement cell. In order to connect the diluting device to the measurement cell, there can also be used a separate adjusting piece or adjusting pieces, so that possible flow defects between the diluting device and the measurement cell can be avoided.

In the diluting device according to the invention, there is installed at least one liquid conduit in order to feed the diluting liquid, so that the liquid conduit is installed essentially symmetrically with respect to the walls of the chamber constituting the diluting device. The liquid conduit is provided with at least one nozzle element, through which the diluting liquid is fed into the liquid contained in the diluting device, so that agitation is created in the liquid in order to efficiently process the solids fed in along with the sample slurry flow before the solids flow into the measurement cell of the analyzer.

When using two chambers in the diluting device, the first chamber of the diluting device is also the upper chamber thereof, and the slurry flow is conducted to the top part of said upper chamber from the sample cutter serving as the sampler. The second chamber of the diluting device, which at the same time is the lower chamber of the diluting device, is mechanically connected to the measurement cell installed underneath the chamber and made of a transparent material. With respect to each other, the first and second chambers of the diluting device are advantageously arranged so that the bottom part of the first chamber is connected to the top part of the second chamber. Two chambers can advantageously be utilized for instance in cases where a remarkable degree of diluting is required. In that case, owing to the larger volume of the two chambers, the diluting is essentially easier.

In shape, the first chamber of the device according to the invention is downwardly narrowing, so that the shape advantageously corresponds to a truncated pyramid or cone, for example, the bottom of said pyramid or cone being the top part of the chamber, and the truncated spot being the bottom part of the chamber. The slurry sample containing the solid material is fed into the first chamber through the top part of the chamber, advantageously onto an inclined surface arranged inside the chamber. The inclined surface is arranged so that it is located above the liquid surface essentially throughout the operation of the device. However, the inclined surface may also be at least partly covered by the liquid fed in the chamber. Through the essentially open top part of the first chamber, in the chamber there is installed at least one liquid conduit for feeding the diluting liquid, so that said liquid conduit extends, through the gap between the first and second chambers, to the second chamber. The liquid conduit is arranged in the middle of the first and second chambers, so that the liquid conduit is in an essentially symmetrical position with respect to the chamber walls. In case for instance two liquid conduits are used, the first liquid conduit can extend only to the first chamber and the second liquid conduit only to the second chamber through the first chamber.

In shape, also the second chamber of the device according to the invention is downwardly narrowing. Advantageously the top part of the second chamber is rectangular, but in area larger than the bottom part of the first chamber. The difference in the areas is advantageously achieved by means of the design of a flange connected to the top part of the second chamber, or, when necessary, by means of a separate adjusting piece.

The downwardly narrowing shape of the second chamber is achieved so that when the top part of the channel is rectangular, two opposite walls are arranged to approach each other towards the solids discharge aperture. On the other hand, the other two opposite walls of the chamber are arranged in an essentially parallel direction with respect to each other. In the bottom part of the chamber, the walls of the second chamber form an aperture that is essentially equal in size as the aperture provided in the top part of the analyzer measurement cell. In addition, the two essentially parallel walls of the second chamber are parallel with the corresponding walls of the analyzer measurement cell. Now the chamber and the measurement cell can be mechanically and directly interconnected, and the solids to be analyzed are discharged from the diluting device according to the invention directly to the measurement cell of the analyzer.

In the device according to the invention, the diluting of the slurry sample is carried out so that the sample slurry flow entering the first chamber is conducted onto the inclined surface, which is washed in an essentially same rhythm as the sample cutter takes a sample of the slurry flow to be analyzed. Thus the washing liquid causes the initial dilution of the sample. The slurry sample is further diluted by feeding diluting liquid to the chambers through nozzles connected to liquid conduits. A first nozzle element connected to a liquid conduit, comprising at least one nozzle, feeds diluting liquid to the center part of the first chamber, so that the diluting liquid circulates in essentially every direction around the liquid conduit. At the same time, the supplied diluting liquid causes agitation in the liquid contained in the chamber, and the delay time of the solids to be analyzed can thus be increased in the chamber, simultaneously diluting the whole sample flow.

In order to boost the agitation of the slurry sample to be diluted, diluting liquid is further conducted, through the same liquid conduit, through a second nozzle element comprising at least one nozzle and connected to the liquid conduit in the center part of the second chamber, essentially in all directions with respect to the liquid conduit. In addition, in order to boost agitation, the cross-sectional area of the flow aperture provided in the top part of the second chamber is made larger than the flow aperture provided in the bottom part of the first chamber.

When using the device according to the invention along with an optical grain size analyzer, it is important that the sample to be analyzed in the measurement cell of the grain size analyzer, which cell is rectangular in cross-section and is directly connected to the bottom part of the second chamber, is essentially homogeneous on the long side of the measurement cell, but a certain degree of nonhomogeneousness in the sample is allowed on the short side of the measurement cell, because the measurement is automatically carried out as an average measurement on the side of the short side. Now in the bottom part of the second chamber, where the agitation is good, there are according to the invention provided essentially high vertical walls that are placed equidistantly with respect to each other, said walls being arranged so that their distance corresponds to the width of the measurement cell on the short sides. On the other hand, the second chamber walls connected to the long sides of the measurement cell are arranged to be drawn apart, so that the heavy solid particles are allowed to fall on the walls and slide down along the long side of the measurement cell.

BRIEF DESCRIPTION OF THE DRAWINGS

The invention is described in more detail below with reference the appended drawing, where.

Figure 1:
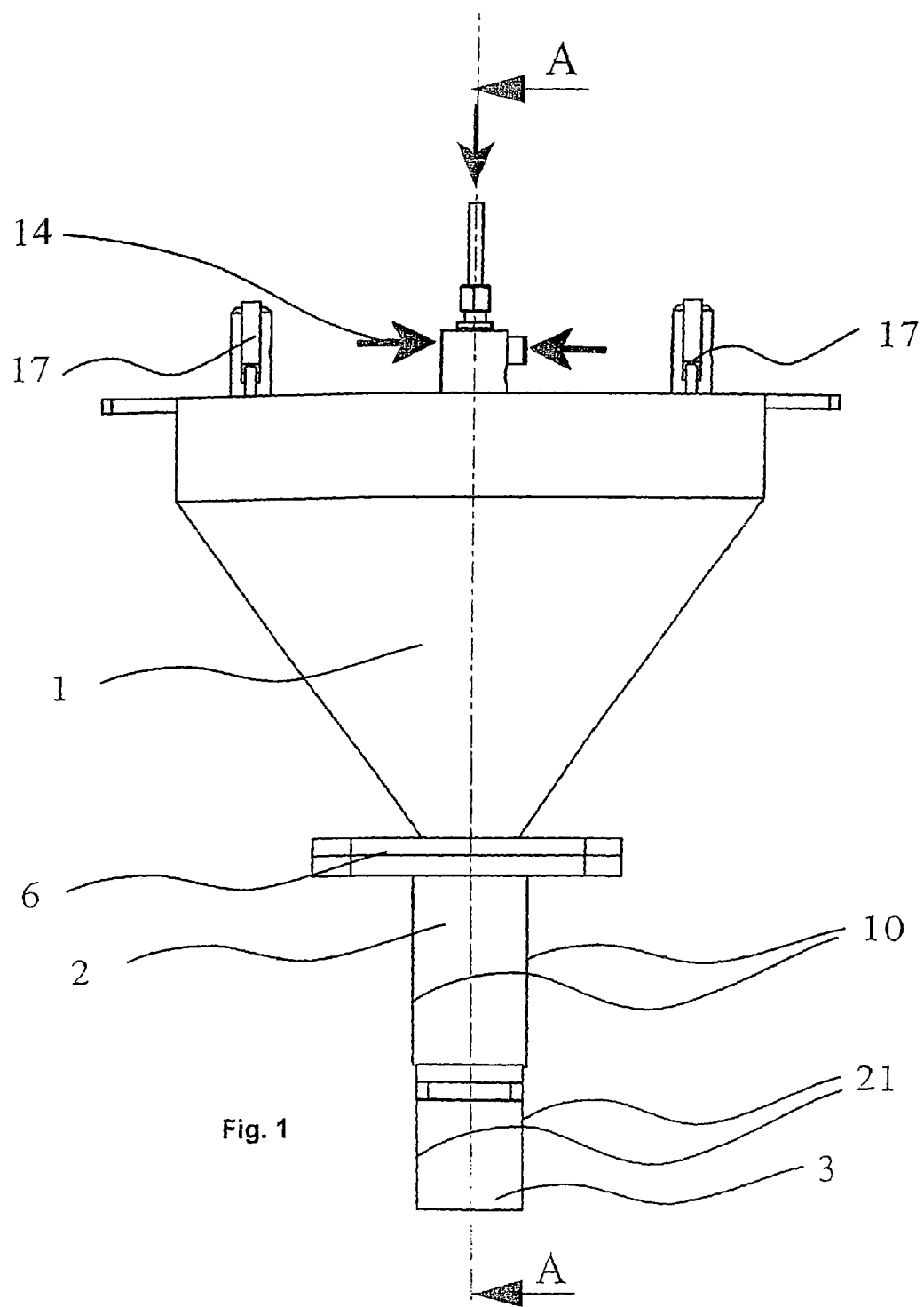
FIG. 1 illustrates a preferred embodiment of the invention, seen from the side.
Figure 2:
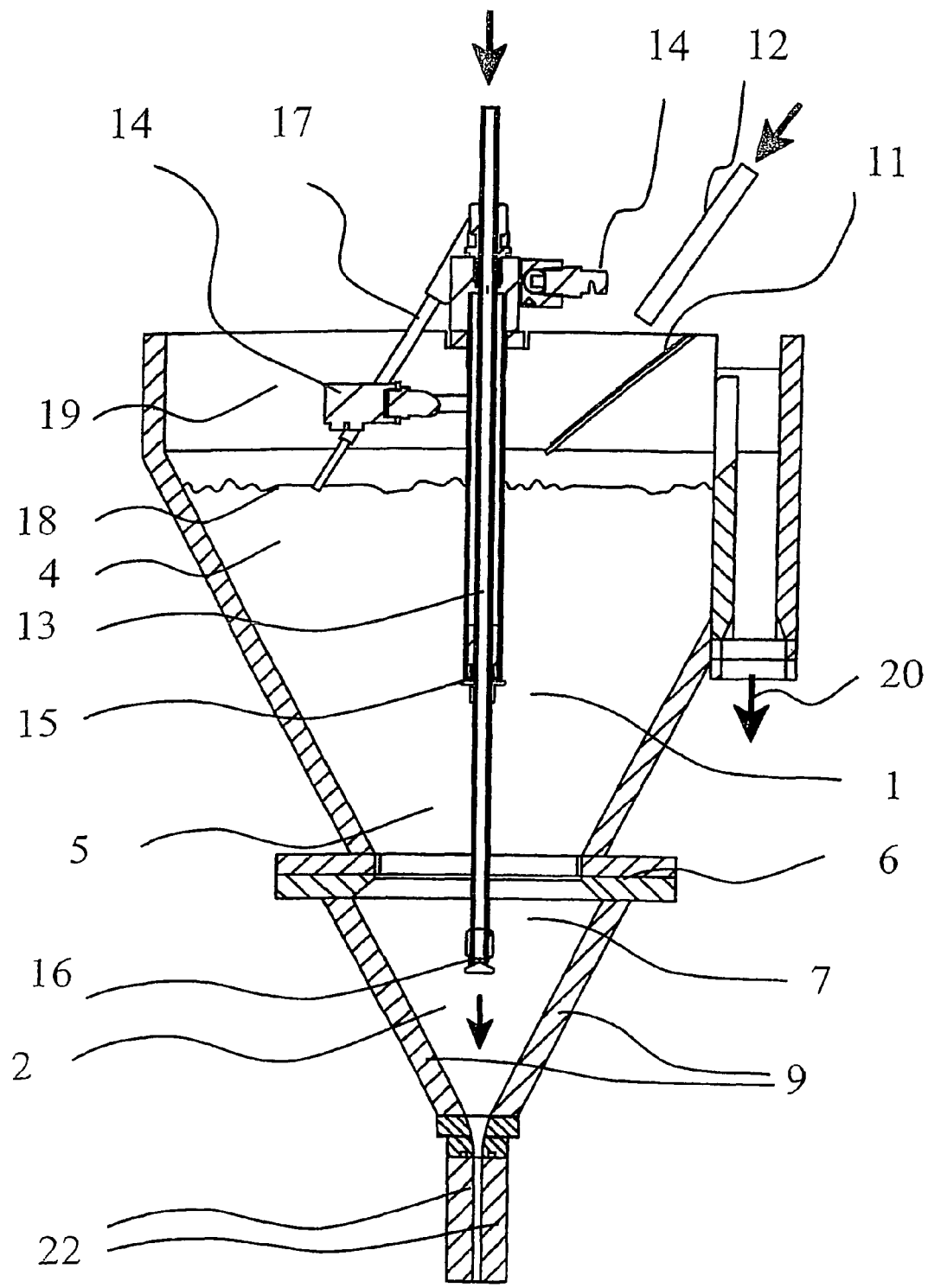
FIG. 2 illustrates an embodiment according to FIG. 1 in partial cross-section, seen from the direction A-A.

According to FIGS. 1 and 2, the diluting device according to the invention comprises two chambers, a first chamber, i.e. the top chamber 1 serving as the slurry sample supply chamber, and a second chamber, i.e. the bottom chamber 2 serving as the discharge chamber of the solids contained in the slurry sample, said chambers being mechanically connected on top of each other in an essentially symmetrical manner. The second chamber 2 is further mechanically connected to a measurement cell 3 of the optical grain size analyzer, said cell being made of glass.

In shape, the top chamber 1 of the device according to the invention is a truncated pyramid and installed so that the bottom of the truncated cone constitutes the top part 4 of the first chamber. In the embodiment illustrated in the drawings, in the top part 4 of the first chamber there is attached an additional element 19, which as such is not absolutely necessary in the device according to the invention. The cutting spot of the pyramid of the first chamber 1 forms the bottom part 5 of the top chamber 1, which bottom part is mechanically connected to the second chamber, the bottom chamber 2. The bottom part 5 of the top chamber is by a flange joint 6 connected to the top part 7 of the bottom chamber. Because the cross-sectional area of the top part 7 of the bottom chamber is larger than the bottom part 5 of the top chamber, the element of the flange joint 6 that is connected to the bottom chamber 2 is designed so that the heavy particles possibly contained in the sample, which particles have fallen on the walls of the first chamber 1 and roll down along said walls, drop into the second chamber 2 and are remixed in the slurry.

The cross-sectional area of the bottom chamber 2 is reduced, when proceeding towards the discharge aperture of the solids contained in the slurry sample, so that the cross-sectional area of the bottom chamber 2 both in shape and in size corresponds to the rectangular cross-sectional area of the measurement cell 3 of the optical grain size analyzer. The bottom chamber 2 comprises four walls, two opposite walls 9 that approach each other, and two opposite walls 10 that are essentially parallel and thus located equidistantly with respect to each other. On the horizontal level according to the drawings, the opposite parallel walls 10 are shorter than the mutually approaching walls 9, and thus the walls 10 are aligned to match the short walls 21 of the measurement cell 3. Respectively, the walls 9 approaching the discharge aperture for the solids contained in the slurry sample are aligned to match the long walls 22 of the measurement cell 3.

In the device according to the invention, in the top part of the top chamber 1, there is installed in an inclined position a sheet 11, and the sample to be analyzed is conducted onto the surface of said sheet through a sample conduit 12 coming from the sample cutter. In addition, through the top part of the top chamber 1, there is installed a liquid conduit 13 inside the device, said liquid conduit extending from the top chamber 1 to the bottom chamber 2. The liquid conduit 13 is installed in the middle part of chambers 1 and 2, so that the liquid conduit 13 is aligned symmetrically with respect to the walls of both the top chamber 1 and the bottom chamber 2.

Through the liquid conduit 13, liquid is conducted via the nozzles 14 onto the surface of the sheet 11 constituting an inclined surface in order to wash the sheet from time to time, and thus in order to initially dilute the sample. In addition, the liquid conduit is provided with nozzle elements 15 composed of one or several nozzles, through which diluting liquid is conducted to the top chamber 1, and with nozzle elements 16 composed of one or several nozzles, through which diluting liquid is conducted to the bottom chamber 2. The nozzle elements 15 and 16 are composed of several nozzles, in which case the nozzles 15 and 16 direct the diluting liquid essentially in all directions around the liquid conduit 13.

When the device according to the invention is in operation, both the bottom chamber 2 and the top chamber 1 are essentially continuously filled with liquid, and in order to adjust the surface of said liquid, the device comprises surface height adjusting elements 17. By adjusting the operation time of the nozzles 14, the liquid surface 18 is essentially maintained on the level defined by the height adjusting element 17. Advantageously the height of the liquid surface 18 is adjusted on a level where the sheet 11 constituting the inclined surface is located above the liquid surface. In preparation for a possible blocking of the measurement cell 3, the additional element 19 connected to the top chamber 1 is provided with a liquid overflow conduit 20.

When the device according to the invention is in operation, the slurry sample obtained from the sample conduit 12 is first conducted onto the surface of the sheet 11 constituting the inclined surface, which surface is then washed by the liquid supplied through the nozzles 14. From the surface of the sheet 11, the slurry flows downwardly to the liquid filling the chambers 1 and 2, where the slurry is diluted and agitated by means of the liquid supplied through the nozzles 15 and 16. On the basis of circulation changes, the solid particles to be analyzed are obtained in an advantageous position with respect to the measurement cell 3 of the grain size analyzer.

Figure 3:
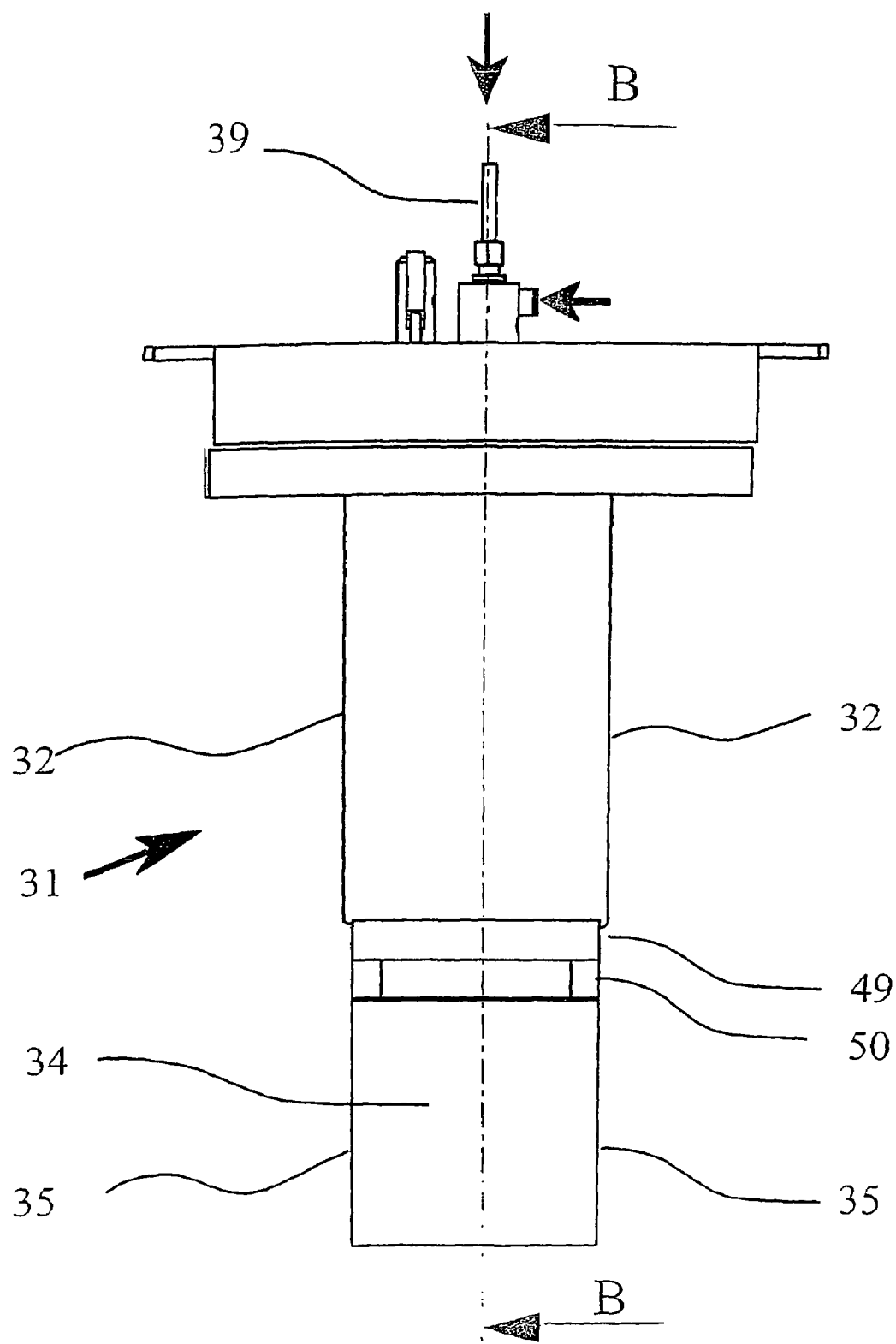
FIG. 3 illustrates another preferred embodiment of the invention, seen from the side
Figure 4:
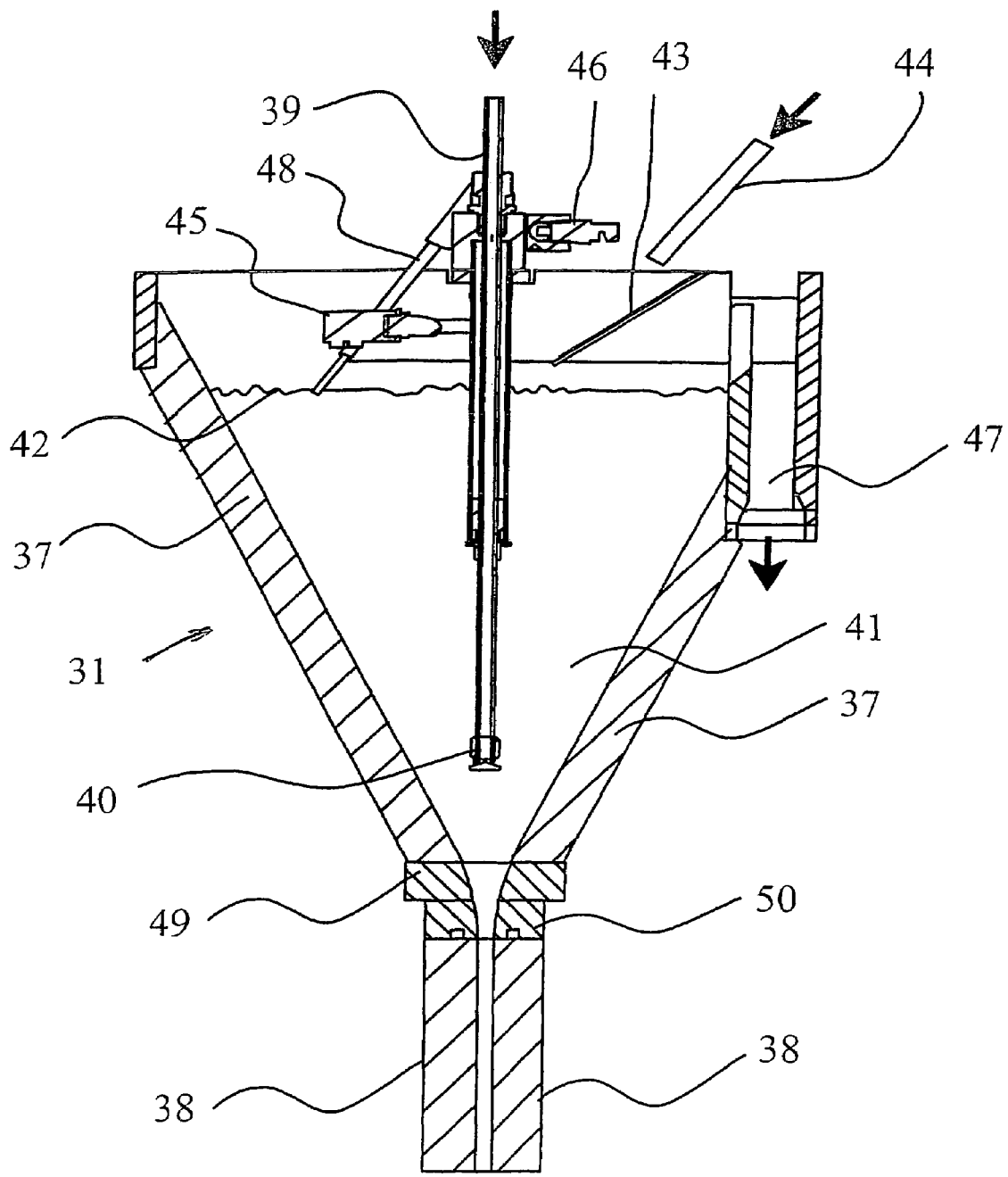
FIG. 4 illustrates an embodiment according to FIG. 1 in partial cross-section, seen from the direction B-B.

According to FIGS. 3 and 4, the diluting device comprises an downwardly narrowing chamber 31, with two opposite walls 32 that are parallel with respect to each other and also parallel with the respective walls 35 of the measurement cell 34 of the analyzer that is connected to the chamber 31. The other two opposite walls 37 of the chamber 31 are mutually arranged so that the walls 37 approach each other when proceeding towards the measurement cell 34. The mutually parallel walls 32 of the chamber 31 are aligned to match the short walls 35 of the measurement cell 34, whereas the mutually approaching walls 37 of the chamber 31 are aligned to match the long walls 38 of the measurement cell 34.

The chamber 31 is provided with a liquid conduit 39 in order to conduct the diluting liquid to the chamber 31. Advantageously the liquid conduit 39 is installed in a symmetrical position with respect to the walls 32 and 37 of the chamber 31. Owing to said symmetrical position, the diluting liquid discharged through the nozzle element 40 installed in the liquid conduit 39 and comprising one or several nozzles is directed in an essentially effective way to the liquid 41 contained throughout the chamber 31 in order to achieve an advantageous agitation. In the top part of the chamber 31, above the liquid surface 42, there is installed an inclined surface 43, to which the slurry sample supplied through the slurry conduit 44 and diluted in the diluting device is conducted. In the vicinity of said inclined surface 43, there also are installed nozzles 45 and 46 in order to feed washing liquid onto the inclined surface 43 in order to wash the slurry sample and to conduct it into the liquid 41 contained in the chamber. In addition, in the chamber 31 there is installed an adjusting element 48 of the liquid surface height. In case the measurement cell should be blocked, the chamber is also provided with an overflow conduit 47. Moreover, between the chamber 31 and the measurement cell 34, there are arranged adjusting pieces 49 and 50 in order to advantageously connect the chamber 31 and the measurement cell 34 to each other.

When the embodiment according to FIGS. 3 and 4 is in operation, the slurry sample that is washed away from the inclined surface 43 is mixed in the liquid 41 contained in the chamber 31, into which liquid there also is fed diluting liquid through the nozzle element 40 connected to the liquid conduit 39 in order to maintain an efficient agitation throughout the operation of the diluting device. Owing to the efficient agitation, the solid particles to be analyzed are obtained in an advantageous position with respect to the measurement cell 34 of the optical grain size analyzer.

The invention claimed is:

1. A device for a continuously operated dilution of a slurry sample, through which device the slurry sample is fed directly into a continuously operated optical analyzer, such as a grain size analyzer, comprising
   a) downwardly narrowing chamber;
   b) elements for feeding the slurry sample into the downwardly narrowing chamber;
   c) elements for feeding diluting liquid into the downwardly narrowing chamber;
   d) elements for removing solids contained in the slurry;
   e) elements for discharging both the liquid contained in the slurry and the liquid used for dilution; and
   f) an analyzer cell;
   wherein the downwardly narrowing chamber is connected to the analyzer measurement cell, and wherein the downwardly narrowing chamber comprises two opposite walls that are essentially parallel both with respect to each other and with respect to the corresponding walls of the analyzer measurement cell.

2. The device according to claim 1, further comprising at least one liquid conduit provided with a nozzle element to feed diluting liquid into the chamber and to agitate the liquid contained in the chamber.

3. The device according to claim 2, wherein the liquid conduit is installed symmetrically with respect to the walls of the chamber.

4. The device according to claim 2, further comprising a second downwardly narrowing chamber, wherein the downwardly narrowing chambers are in liquid connection with each other and are at least partly filled with liquid.

5. The device according to claim 4, wherein the first and second chambers of the device are mutually arranged so that the bottom part of the first chamber is connected to the top part of the second chamber.

6. The device according to claim 4, wherein the cross-sectional area of the top part of the second chamber is larger than the cross-sectional area of the bottom part of the first chamber.

7. The device according to claim 4, wherein the liquid conduit includes nozzle elements comprising at least one nozzle for feeding diluting liquid into both chambers to advantageously agitate the liquid contained in the chambers.

* * * * *